United States Patent [19]

Tucker et al.

[11] Patent Number: 5,254,346
[45] Date of Patent: Oct. 19, 1993

[54] OCCLUSIVE BODY FOR ADMINISTERING A PHYSIOLOGICALLY ACTIVE SUBSTANCE

[76] Inventors: Mark J. Tucker, Round Steps, High Street, Stow-on-the-Wold, Gloucester GL54 1DL, United Kingdom; Mark R. Tucker, P.O. Box 23530, Bahrain, Bahrain

[21] Appl. No.: 555,463
[22] PCT Filed: Feb. 23, 1989
[86] PCT No.: PCT/GB89/00185
 § 371 Date: Aug. 17, 1990
 § 102(e) Date: Aug. 17, 1990
[87] PCT Pub. No.: WO89/07959
 PCT Pub. Date: Sep. 8, 1989

[30] Foreign Application Priority Data

Feb. 23, 1988 [GB] United Kingdom ............... 8804164

[51] Int. Cl.⁵ .................................................... A61F 13/00
[52] U.S. Cl. ................................ 424/449; 424/434; 424/448
[58] Field of Search ...................... 424/448, 449, 434

[56] References Cited

U.S. PATENT DOCUMENTS

| | | | |
|---|---|---|---|
| 3,598,122 | 8/1971 | Zaffaroni | 128/268 |
| 4,067,961 | 1/1978 | Laughlin | 424/15 |
| 4,597,961 | 7/1986 | Etscorn | 424/28 |
| 4,725,272 | 2/1988 | Gale | 424/448 |
| 4,752,478 | 6/1988 | Bondi | 424/449 |
| 4,756,710 | 7/1988 | Bondi | 424/449 |
| 4,764,382 | 8/1988 | Kydonieus | 424/449 |

FOREIGN PATENT DOCUMENTS 0197504 10/1986 European Pat. Off.
0208395 1/1987 European Pat. Off.
2174605 11/1986 United Kingdom.

OTHER PUBLICATIONS

O'Neill et al. Development and evaluation using hairless mouse skin of a transdermal timolol product, Int. J. Pharmaceutics, 48 pp. 247-254, 1988.

Primary Examiner—Thurman K. Page
Assistant Examiner—D. Gabrielle Phelan
Attorney, Agent, or Firm—Shoemaker and Mattare Ltd.

[57] ABSTRACT

An occlusive body such as a patch, pad or bandage is provided which incorporates a reservoir (5) containing a physiologically active substance, the reservoir incorporating a membrane permeable to the active substance and either the membrane being hydrophilic and the reservoir contents being hydrophobic or vice-versa. The reservoir also contains a filler material such as methyl cellulose which immobilizes the reservoir contents by forming a gel. The dosage rate of the active substance through the membrane, when the latter is applied to the skin of a subject, is substantially constant until much of the dose has been delivered from the reservoir.

33 Claims, 7 Drawing Sheets

OCCLUSIVE BODY FOR ADMINISTERING A PHYSIOLOGICALLY ACTIVE SUBSTANCE

This invention relates to an occlusive body (such as a patch, pad or bandage for example) for the transdermal administration of a physiologically active substance (by attachment to the skin or a buccal membrane for example) at a controlled rate over an extended period. In U.S. Pat. No 3,598,122 (Zaffaroni) there was disclosed a bandage for use in the continuous administration of systemically active drugs by absorption through the skin or oral mucosa.

U.S. Pat. No. 3,598,122 disclosed a broad range of systemically active drugs which could be employed, and indicated that any systemically active drug which is absorbed by the body surface beneath the bandage could be employed. The substances disclosed as being suitable for incorporation in the bandage included antimicrobial agents such as penicillin, tetracycline, oxytetracycline, chlortetracycline, chloramphenicol, and sulfonamides; Sedatives and Hypnotics such as pentabarbital sodium, phenobarbital, secobarbital sodium, codeine, ($\alpha$ bromoisoaleryl) urea, carbromal, and sodium phenobarbital; Psychic Energizers such as 3-(2-aminoprophyl) indole acetate and 3-(2-aminobutyl) indole acetate; Tranquilizers such as reserpine, chlorpromazine hydrochloride, and thiopropazate hydrochloride; Hormones such as adreno-corticosteroids, for example, 6-methylprednisolone, cortisone, cortisol, and triamcinolone; androgenic steroids, for example, methyltestosterone, and fluoxymesterone, estrogenic steroids, for example, estrone, 17$\beta$-estradiol and ethinyl estradiol; progestational steroids, for example 17-hydroxyprogesterone acetate, medroxyprogesterone acetate, 19-norprogesterone, and norethindrone; and thyroxine; Antipyretics such as aspirin, salicylamide, and sodium salicylate; Antispasmodics such as atropine, methscopolamine bromide, methscopolamine bromide with phenobarbital; Antimalarials such as the 4-aminoquinolines, 8-aminoquinolines, and pyrimethamine; and Nutritional agents such as vitamins, essential amino acids, and essential fats.

The bandage comprised a backing member having on one surface thereof a reservoir containing a systemically active drug. The reservoir had a wall distant from the backing member and permeable to the passage of the drug. A pressure-sensitive adhesive layer, also permeable to passage of the drug, was carried by the reservoir. The drug was in a form acceptable for absorption through the skin or the mucosa of the mouth. It was explained that the percutaneous rather than oral route enabled continuous administration of the drug over a period of time, and for this purpose fibrous masses and fabrics that merely absorbed and released drug solutions in a gross and uncontrollable manner were to be avoided.

It was indicated that the percutaneous route had the advantage over the oral route of drug administration that uncertainties in the rate of dosage through the gastrointestinal tract (depending on the amount and type of food eaten, for example) were avoided. Also, charge peaks in the drug concentration in the bloodstream were thereby avoided.

The materials used to form the reservoir could also form the membrane, and suitable materials included organopolysiloxane rubbers, hydrophilic polymers of monoesters of an olefinic acid such as acrylic acid and methacrylic acid, polyvinylalcohol, polyvinylacetate, plasticised nylon, collagen, modified collagen, gelatin, and waxes such as polyethylene wax. An exemplary bandage contained megesterol acetate powder within a reservoir of dimethyl silicone rubber, which was stated to be effective over a 24 hour period. No liquid was present within the reservoir.

However U.S. Pat. No. 3,598,122 did indicate that drugs which in isolation do not pass through the skin could be dissolved in absorbable pharmacologically acceptable solvents such as $C_2$ to $C_{10}$ alcohols, $C_5$ to $C_{12}$ hydrocarbons, $C_4$ to $C_{10}$ aldehydes and ketones, $C_4$ to $CF_{10}$ esters, ethereal oils, halogenated hydrocarbons and mixtures of the above.

Furthermore, U.S. Pat. No. 3,598,122 taught that by varying the composition and thickness of the reservoir wall the dosage rate per area of bandage can be controlled, since the reservoir wall acts as a solubility membrane to meter the flow or diffusion of the drug.

One material disclosed as being suitable for the reservoir wall was a hydrophilic polymer of an ester of an olefinic acid.

U.S. Pat. No. 3,946,106 which is incorporated herein by reference discloses a pharmaceutical delivery device suitable for implantation in the body and comprising a silicone polymer matrix which incorporates closed microscopic compartments of dimensions 10 to 200 micrometers. The matrix is formed by cross-linking a liquid precursor of the polymer in an emulsion of the pharmaceutical in a hydrophilic solvent system and the closed microscopic compartments of the resulting polymer accordingly contain a solution of the pharmaceutical in the solvent. The solvent system may comprise 30% to 60% polyethylene glycol, which results in a constant rate of release of the pharmaceutical when the device is in an aqueous environment. The silicone polymer matrix may optionally be enclosed within a sealed or unsealed polymer container, e.g. of heat-shrunk polyethylene film. It is stated at Column.9, lines 11 to 15 that exposing the silicone polymer matrix "advantageously increases the rate of pharmaceutical release" and results "in a higher but constant rate of release". Thus the teaching of this patent is that the properties of the outer polymer film or container are not responsible for the constant (i.e. zero order) rate of release of the pharmaceutical in an aqueous environment. There is no indication in this patent that the rate of release would be zero order in a non-aqueous environment—e.g. on the surface of the skin, and such a zero order release into the skin has not been demonstrated.

U.S. Pat. No. 4,336,243 (which is incorporated by reference) discloses a pad for the transdermal delivery of nitroglycerine comprising a silicone polymer matrix containing a solution of nitroglycerine in closed microcompartments thereof. No outer membrane or surfactant is disclosed. The solvent system comprises water, polyethylene glycol (a hydrophilic solvent) and a hydrophobic solvent which is mineral oil or a triglyceride and the rate of release of the nitroglycerine is alleged to be constant. It will be noted that U.S. Pat. No. 4,336,243 is a later patent than U.S. Pat. No. 3,946,106 which is specifically directed to the problem of transdermal delivery, and differs therefrom by the incorporation of a hydrophobic solvent component in the closed microcompartments of the polymer matrix.

The percutaneous administration of nicotine by means of an occlusive pad in a dose approximating that delivered by a variety of nicotine-containing products was described in U.S. Pat. No. 4,597,961 (Etscorn). A typical pad had a reservoir defined by a cavity within a backing sheet and filled with 1-4 microliters of nicotine base. The nicotine in the reservoir was separated from the skin by a microporous nicotine-permeable membrane, but no directions were given about what kind of membrane should be used, nor any directions concerning the relationship between the membrane and the reservoir materials. In another pad disclosed: U.S. Pat. No. 4,597,961, nicotine base was absorbed in fibrous or porous material which was held in an open reservoir in the bandage. In use, the nicotine wicked from the porous material as it diffused through the skin.

U.S. Pat. No. 4,752,478 EP-A-186071 (which are incorporated herein by reference) disclose a patch for the transdermal delivery of timolol comprising a rate-controlling microporous membrane having an adhesive layer on one major surface thereof and a reservoir of timolol and carrier material in contact with its other major surface. The reservoir comprises an impermeable backing member which is sealed around its periphery to the microporous membrane.

The carrier material may be a semi-solid material such as mineral oil gelled with polyethylene, polyisobutylene, aluminium stearate, propylene glycol or a fatty acid ester, or may be a solid such as silicone, acrylic adhesive, and plasticised polyvinylchloride.

The microporous membrane may be microporous polypropylene, microporous nylon or microporous polycarbonate. EP-A-186071 also discloses rate-controlling membranes of non-microporous material, namely silicone, ethylene vinyl acetate and polyurethane.

It will be noted that nearly all the membrane materials and carrier materials disclosed in EP-A-186071 are hydrophobic. Particular membrane material-carrier material combinations disclosed in EP-A-186071 include:

| Carrier material | Membrane material |
|---|---|
| gelled mineral oil | microporous polypropylene<br>ethylene vinyl acetate<br>silicone<br>polyurethane |
| gelled mineral oil | polyisobutylene + mineral oil<br>microporous polypropylene |

There is no disclosure of a hydrophobic carrier material in combination with a hydrophilic membrane material, nor is there any disclosure of a hydrophilic carrier material in combination with a hydrophobic membrane material.

It is stated in EP-A-186071 that the drug timolol may be administered by the disclosed patches at "a controlled low zero order rate" (p. 2 lines 15 and 16). However an equation given subsequently in the description indicates that the flux through the membrane (and hence the rate of transdermal delivery of the timolol) is proportional to the timolol concentration in the reservoir. Accordingly it is clear that the rate of transdermal delivery of timolol from the patches of EP-A-186071 is zero order (if at all) only over a small proportion of the dose.

An object of the present invention is to provide a system for the transdermal delivery of a physiologically active substance in which the rate of delivery of the active substance is more nearly constant and/or in which the rate of delivery of the active substance is substantially constant over a greater proportion of the total dose contained in the reservoir, in comparison with systems of the prior art.

Unexpectedly, it has now been discovered that the dosage rate of a physiologically active substance from a reservoir through a membrane permeable to that substance may be linearised by providing that either of the following conditions is satisfied, namely:

a) said membrane is hydrophobic and said reservoir contains a hydrophilic wetting agent; or b) said membrane is hydrophilic and said reservoir contents are hydrophobic.

Accordingly the present invention provides an occlusive body for the transdermal administration of a physiologically active substance, said body comprising an impermeable backing and a microporous membrane which define a cavity therebetween, said physiologically active substance being contained within said cavity in liquid form, said microporous membrane being permeable to and in contact with said physiologically active substance and the liquid material confined between said impermeable backing and said microporous membrane within said cavity being substantially immobilised by a viscous flowable gel, characterised in that either;

a) said 30 membrane is hydrophilic and the contents of said cavity are hydrophobic; or b) said membrane is hydrophobic and said cavity contains a hydrophilic wetting agent;

whereby in use, passage of said physiologically active substance through said microporous membrane is rate-controlling and said physiologically active substance is released from said microporous membrane at a rate that is substantially constant over a period of hours.

In another aspect the invention provides an occlusive for the transdermal administration of a physiologically active substance, said body comprising an impermeable backing and a permeable membrane which define a cavity therebetween, said physiologically active substance being contained within said cavity in liquid form, said permeable membrane being capable of adsorbing and desorbing said physiologically active substance and the liquid material confined between said impermeable backing and said permeable membrane within said cavity being substantially immobilised by a viscous flowable gel, characterised in that either:

a) said membrane is hydrophilic and the contents of said cavity are hydrophobic; or b) said membrane is hydrophobic and said cavity contains a hydrophilic wetting agent;

whereby in use, passage of said physiologically active substance through said permeable membrane is rate-controlling and said physiologically active substance is released from said permeable membrane at a rate that is substantially constant over a period of hours.

In International Journal of Pharmaceutics, 48 (1988) pp 247 to 254, (published after the priority date of the present application) C. T. O'Neill et al disclose in vitro arrangements for transdermally administering timolol base from both hydrophobic and hydrophilic reservoirs via various rate-controlling permeable membranes, including both hydrophobic and hydrophilic membranes. Hairless mouse skin is used as a model for human skin. In FIG. 3 of this paper a plot of drug penetration:time is given for a reservoir containing 4% sodium carboxymethyl-cellulose (hydrophilic) in combination with three hydrophobic microporous membranes (Celguard (Reg.Trade Mark) 2400, 2402 and 2412 respectively) and two non-microporous membranes, namely Silastic and EVA. These last two membranes are shown to result in a very low dose rate but the three Celguard membranes each show a substantially linear (zero'th order) dose rate over eight hours and thereby support the teachings of the present invention.

A preferred embodiment of the present invention is in the form of an occlusive pad or patch for attachment to the skin or to a buccal surface to administer a physiologically active substance transdermally, said patch comprising an impermeable backing and a membrane defining therebetween a cavity containing a liquid, characterised in that either (a) the membrane is of a hydrophobic microporous polymer and that the liquid in the cavity is hydrophilic or (b) the membrane is of a hydrophilic microporous polymer and the material in the cavity is hydrophobic, so that the active substance is released at a rate that is substantially constant (e.g. ±20% preferably ±10% or less) over a period of hours (e.g. 5 hours).

Without wishing to be bound by any theory of the present invention, it is believed that in use, the physiologically active substance tends to concentrate near the permeable membrane as a result of the mutual repulsion between the hydrophilic (or hydrophobic) membrane and the hydrophobic (or hydrophilic) material in the reservoir. This concentration gradient is stabilised by the filler material and ensures a steady rate of diffusion of the active substance through the membrane, largely unaffected by the concentration in the bulk material in the reservoir.

If the active substance is a solid it may be dissolved in a solvent which is miscible with the active substance at least to a degree.

In preferred embodiments in which the membrane is hydrophobic and the reservoir contents comprise a hydrophilic wetting agent, the solvent should be essentially hydrophobic to enable it to pass through the membrane with the dissolved active substance, but should be sufficiently hydrophilic to mix with the reservoir material.

It will be noted that the active substance in the occlusive body of the present invention should be in liquid form in order to permeate through the membrane. In some cases the active substance will be liquid at ambient temperature and optionally may be diluted with a physiologically compatible solvent in order to control its rate of diffusion through the membrane. In other cases the active substance will be solid at ambient temperatures and a solvent will be essential in order to bring at least some of the active substance into solution so that it can diffuse through the membrane. It will be noted that the invention includes within its scope an occlusive body (as specified above) in which the active substance is partially in solution ("liquid form") and partially in solid form in contact with the solution.

In general, where a solvent is used to dilute the active substance or to bring a normally solid active substance into solution, the tendency of the active substance to be released from solution and to flow through the membrane will depend on the difference between the solubility parameters $\delta$ of the active substance and solvent. The greater the difference in solubility parameters $\delta$, the greater the rate of permeation through the membrane. In J. Soc. Cosmet. Chem., 36 pp. 319 to 333 (September/October 1985) "Using solubility parameters in cosmetics formulation" - C. D. Vaughan, the solubility parameters of over 150 materials are listed, the solubility parameter $\delta$ being defined as follows:

$$\delta = \frac{\sqrt{23.7\, T_B + 0.02\, T_B^2 - 2950 - 1.986\, K_o}}{MW/\text{density}}$$

where:

$T_B$ = boiling point at one atmosphere (in Kelvin)

$K_o$ = temperature (in Kelvin) at which the density measurement is taken

MW = molecular weight (in grams), the units of density being g/cm$^3$, and subject to the provisions that if the substance is an alcohol then a value of 1.4 is added to the value obtained from the above formula, if the substance is an ester then a value of 0.6 is added to the value obtained from the above formula and if the substance is a ketone having a boiling point above 100° C. then a value of 0.5 is added to the value obtained from the above formula.

The above definition is based upon a widely accepted formula due to J. H. Hildebrand (JACS 38 pp 1442-1473 (1916) and is embodied in a computer program for calculating solubility parameters which is given in the above-mentioned article by Vaughan. In the present application, the term "solubility parameter" is to be understood to mean the term in accordance with the above definition (including the provisos) but if the definition is not applicable (e.g. because the boiling point of the substance cannot be measured owing to decomposition), then any other generally accepted definition may be employed, such as those given on pp 326 and 327 of the above-mentioned article by Vaughan, for example.

The solubility parameter (as defined above) of a solvent may be a tentative guide to its suitability for use with a given active substance whose solubility parameter is known. In general, suitable solvents will tend to be somewhat hydrophobic, if a hydrophobic membrane is used, or somewhat hydrophilic in the case that a hydrophilic membrane is used, and will typically have a solubility parameter $\delta$ of 8 to 11. However, it should be noted that some solvents which do not have a solubility parameter within this range may be suitable and that other solvents which do have a solubility parameter within this range may be unsuitable.

A preferred embodiment of the invention is described below by way of the following non-limiting example, and with reference to FIG. 1 of the accompanying drawings.

EXAMPLE 1

A layer of Dow Corning X7-2910 BIO PSA (Registered Trade Mark) pressure-sensitive adhesive of 35 um thickness was formed on a 75 um thick sheet of Akrosil BIO RELEASE (Registered Trade Mark) release liner by applying a single coating of a 21 wt % solution in freon of the adhesive and allowing the coating to dry.

A 3M MSP 80487 hydrophobic microporous polyethylene membrane of Gurley No. 2856 seconds and thickness 45.7 um (1.8 mils) was then laminated onto the coated face of the release liner.

A nicotine formulation was made by mixing 4.95 g of nicotine base (supplied by BDH Ltd) with 0.05 g of Tea Tree Oil (supplied by De Monchy Ltd). A gel was made comprising 5 wt % "high substitution" grade methyl cellulose (supplied by BDH Ltd) in water. All the nicotine base/Tea Tree Oil mixture was then mixed with 95 ml of the methyl cellulose gel. The resulting formulation remained in the form of a gel.

Approximately 200 mg of the above nicotine formulation was then applied in a "blob" to the microporous polyethylene membrane of the laminate. A sheet of 3M Scotchpak (Registered Trade Mark) aluminised polyester backing material (having a depression formed therein to accommodate the nicotine formulation) was applied to the microporous membrane of the laminate and heat sealed thereto around the periphery of the depression to enclose the nicotine formulation.

The resulting patch had dimensions of approximately 50 mm × 40 mm in the plane of the laminate and contained approximately 10 mg of nicotine base.

Figure 1:
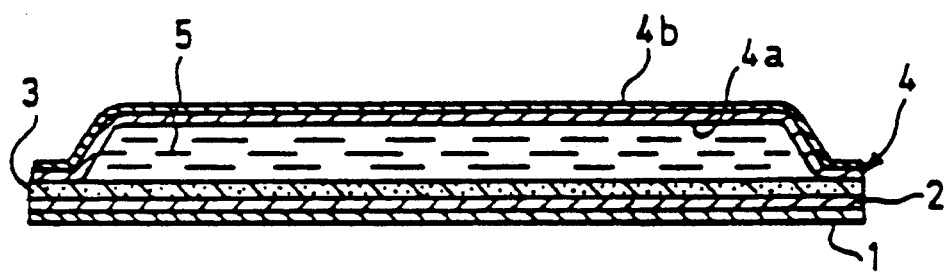
FIG. 1 is a schematic cross-section of the patch of Example 1.

The patch of Example 1 is shown in FIG. 1 which is a schematic cross-section.

The microporous hydrophobic membrane 3 is shown heat-sealed around the periphery of its upper face to the polyester face 4a of a backing sheet 4, which is provided on its outer face with an aluminised layer 4b. Nicotine formulation 5 in the form of a gel is enclosed within a closed body formed by membrane 3 and backing sheet 4 and tends to permeate through membrane 3 and a layer 2 of pressure-sensitive adhesive which is coated on the lower face of the membrane.

Prior to use, such permeation is prevented by release liner 1. Release liner 1 may be stripped from the adhesive layer 2 immediately prior to use and the patch may be adhered to the skin (e.g. of the arm) of a user by the exposed pressure-sensitive adhesive.

The design for other patches using powdered drugs such as paracetamol, ephedrine, or fentanyl may be as for nicotine, except that the drug in an acceptable solvent may be substituted for nicotine. The physiologically active substance may also be clonidine, hyoscine, oestradiol, progesterone, salbutamol or testosterone for example. The adhesive should be selected to ensure that it does not hinder the passage of the active ingredients. The solvent should be sufficiently hydrophobic to pass through the membrane.

Nitroglycerine and other liquid drugs such as timolol for example may be substituted directly for nicotine. Again, it may be necessary to alter the adhesive specification to ensure compatibility, and to use a membrane having a different permeability to ensure an appropriate dosage rate.

Figure 2:
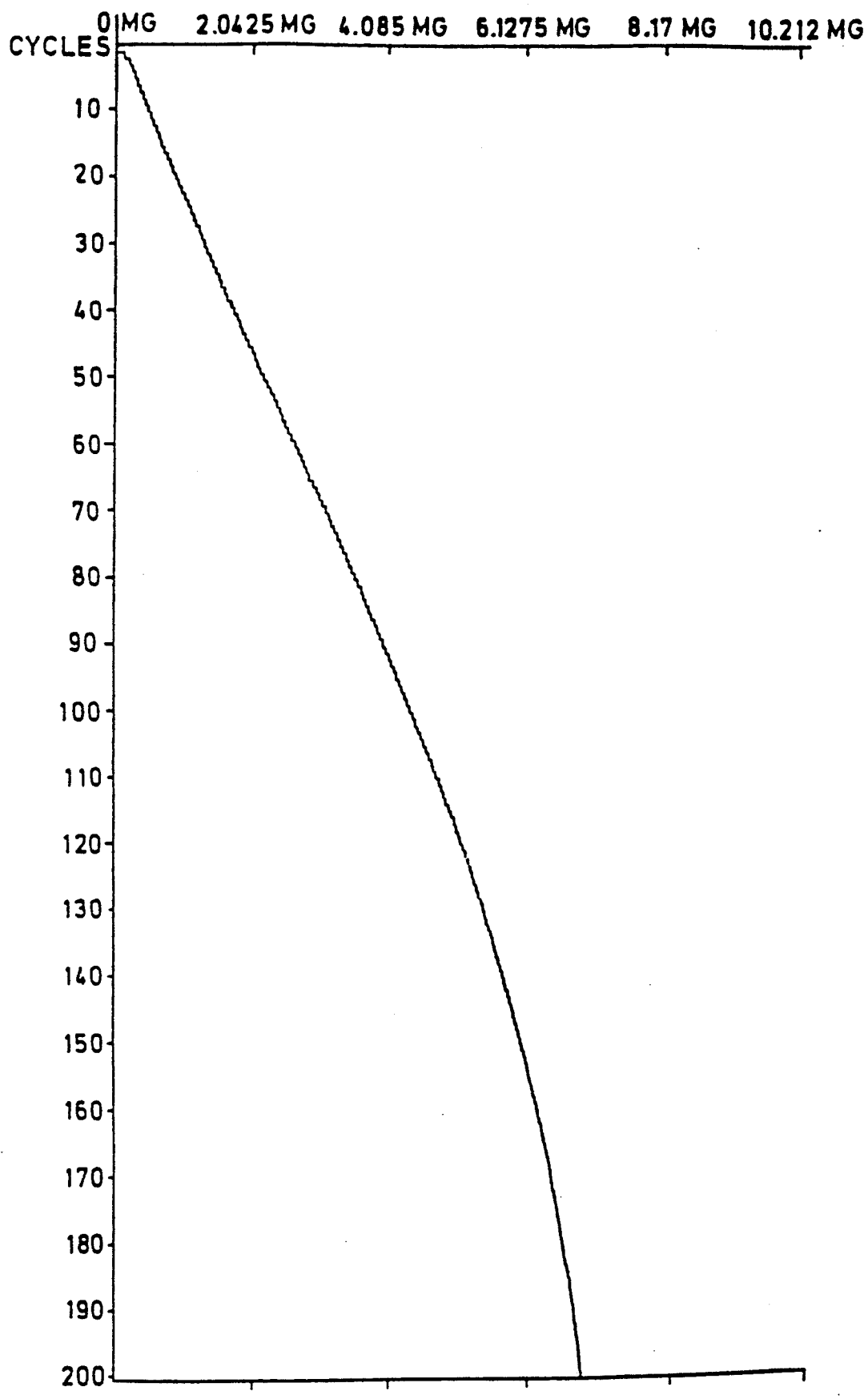
FIGS. 2 to 7 are graphs of release against time for 200 3-minute measurement cycles.
Figure 3:
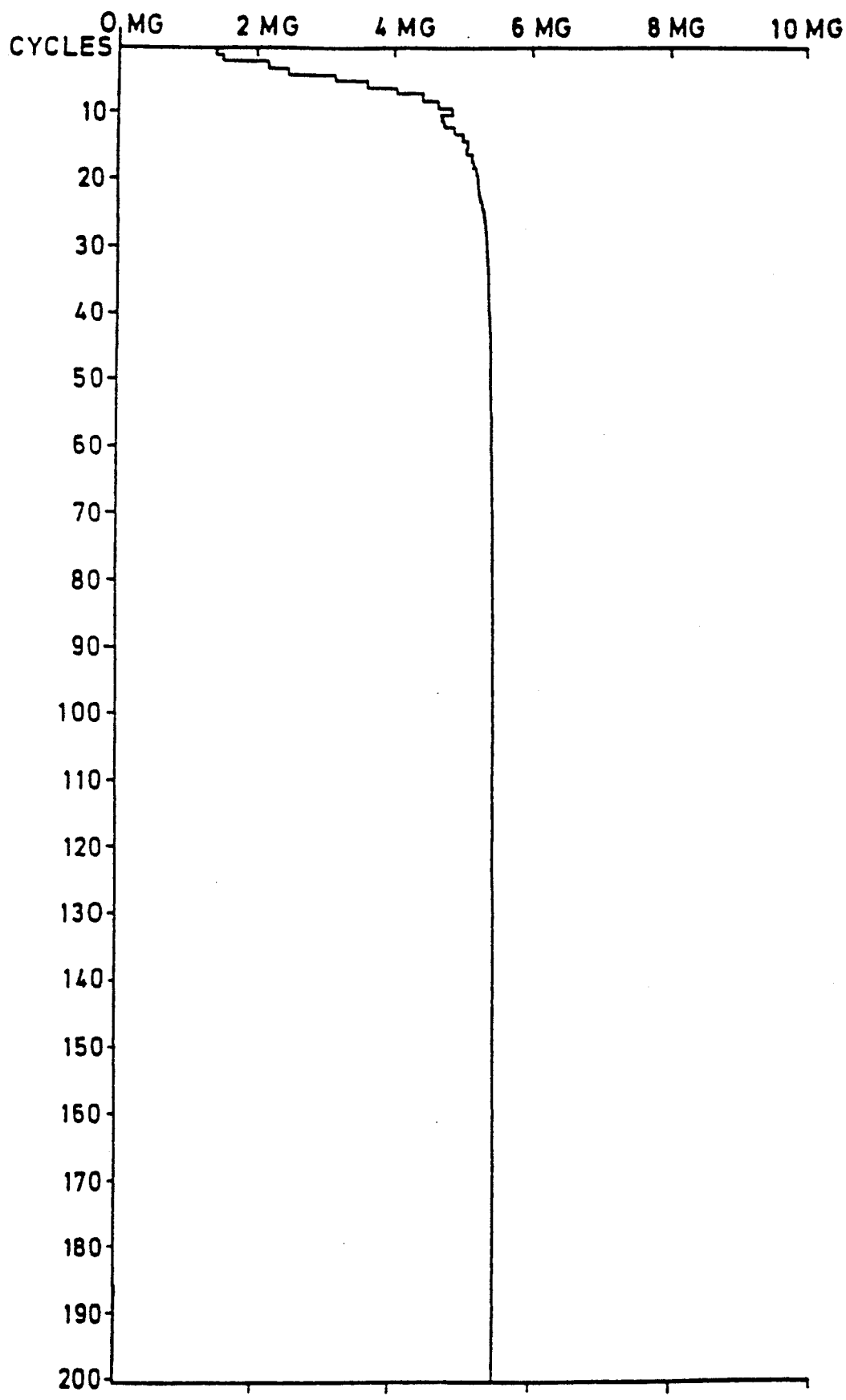
Figure 4:
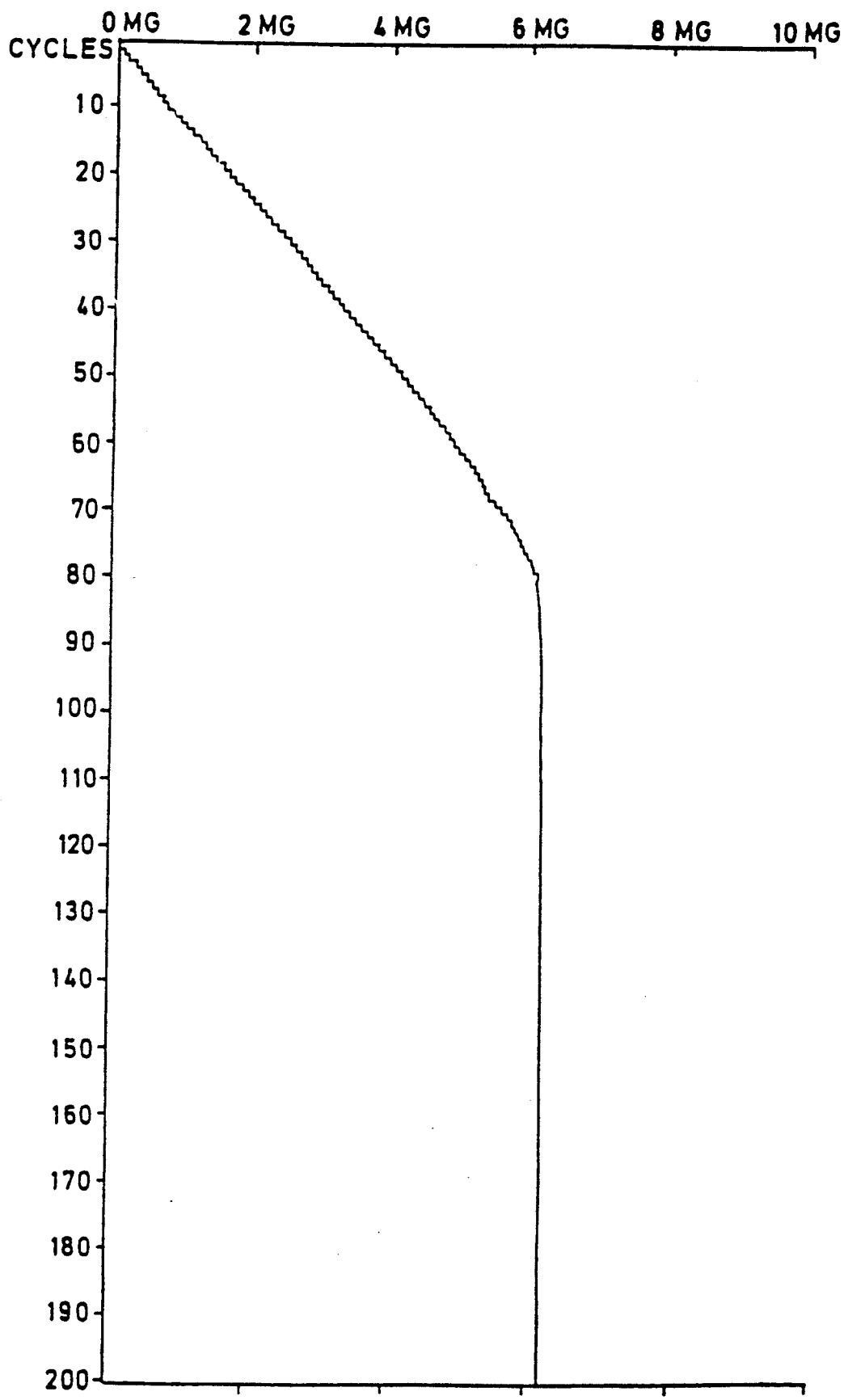
Figure 5:
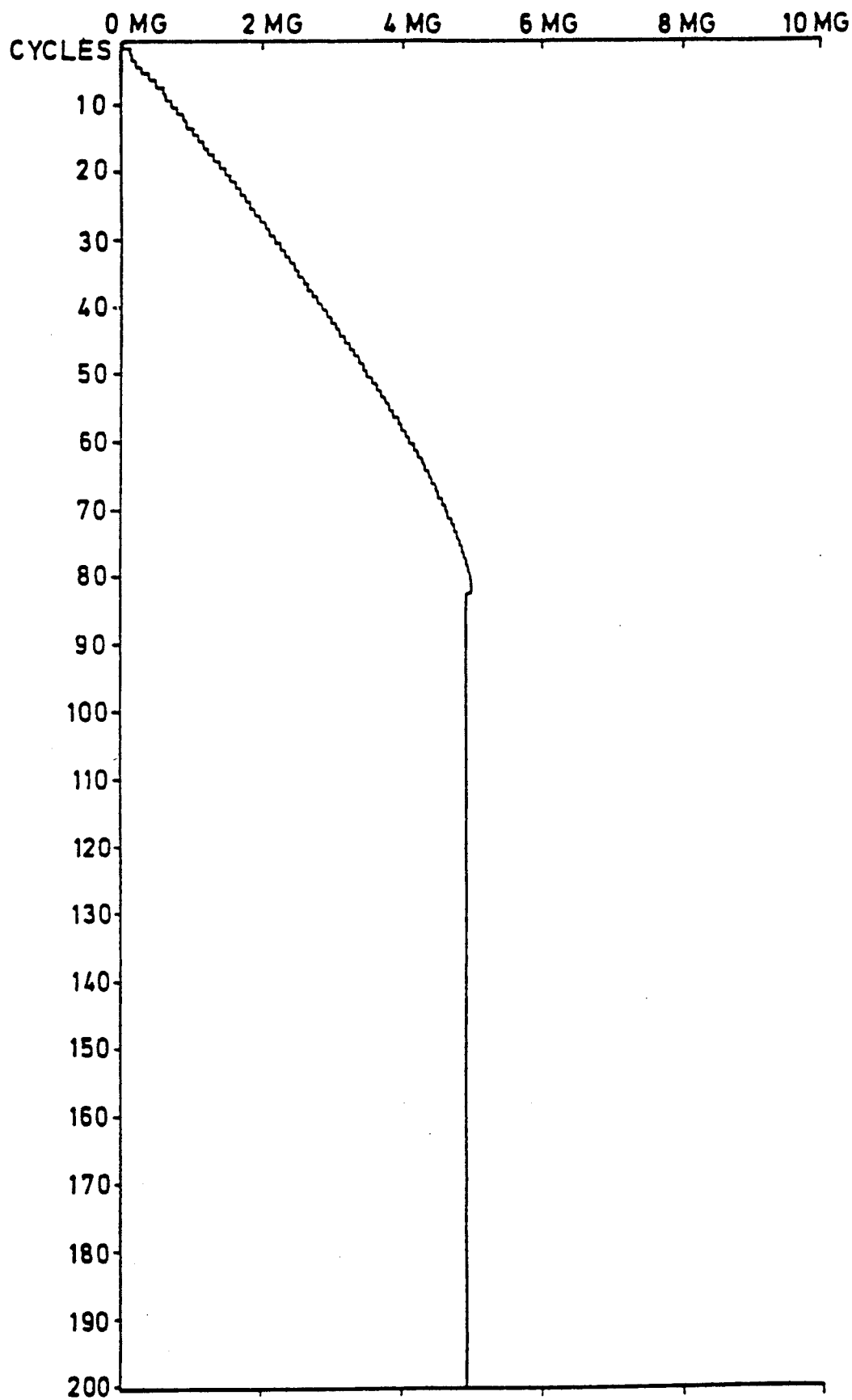
Figure 6:
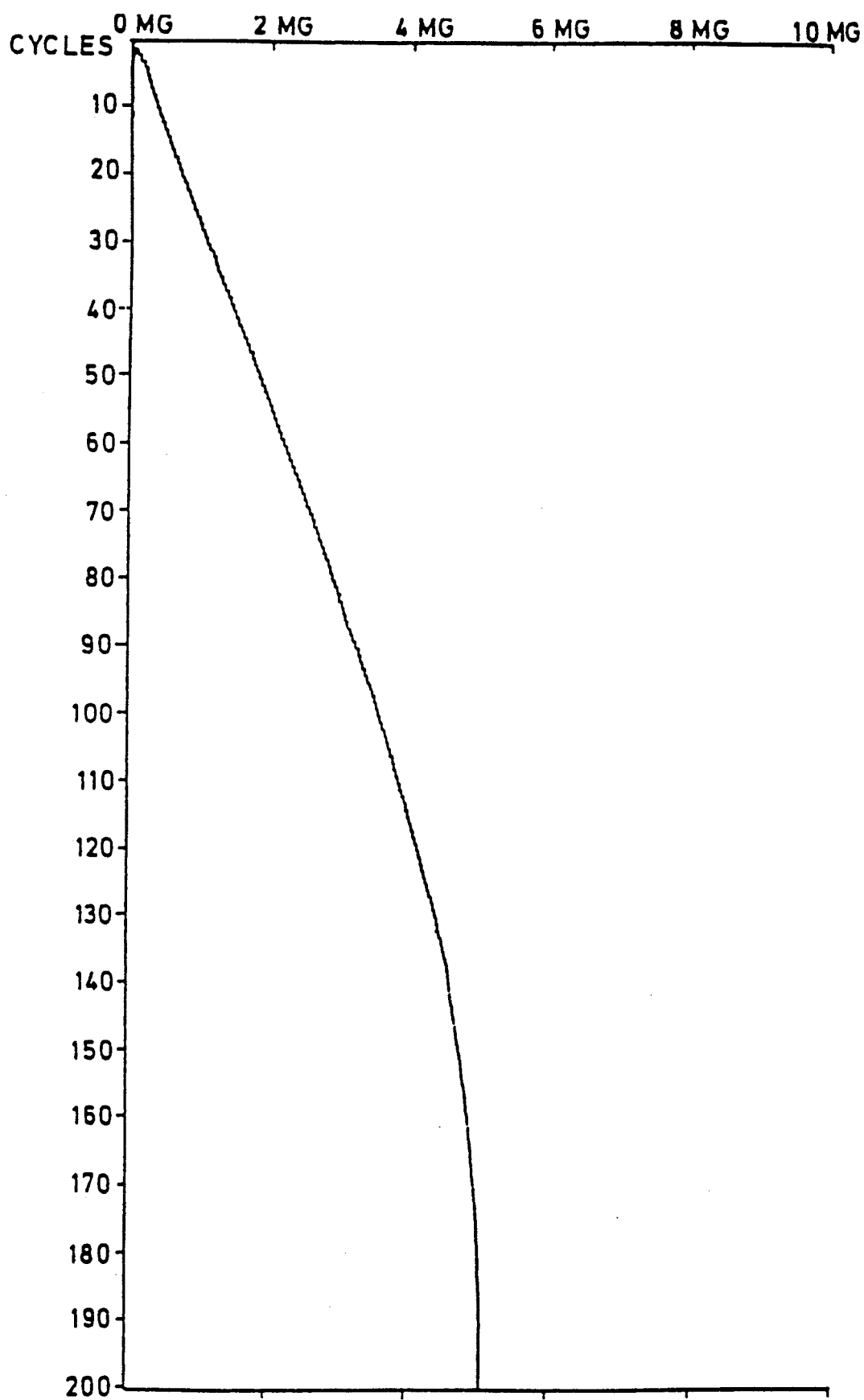
Figure 7:
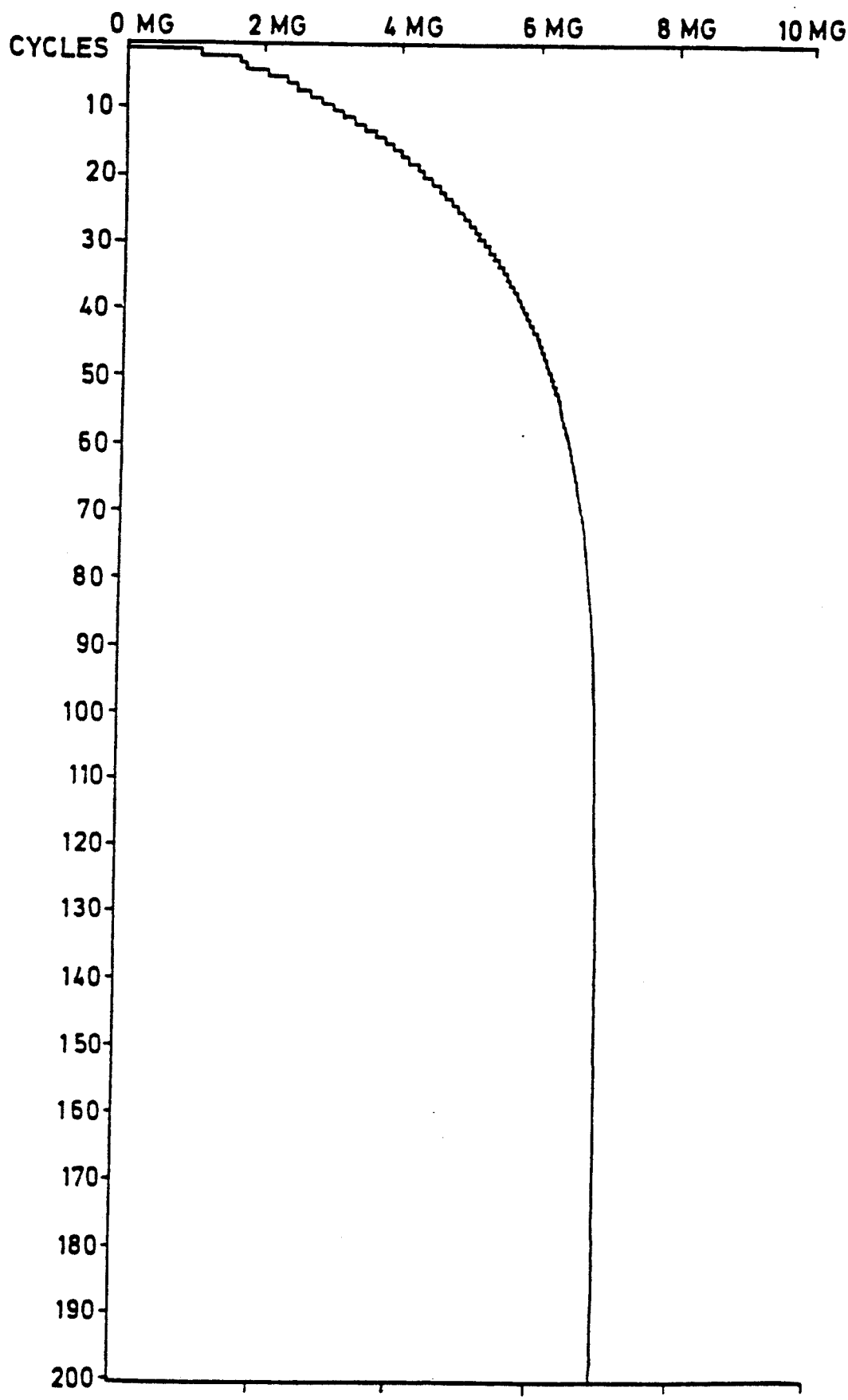

The invention is further illustrated by way of example only in the attached FIGS. 2-7, which are graphs of release against time for 200 3-minute measurement cycles. FIG. 2 shows the release of nicotine from a methyl cellulose reservoir through a microporous hydrophobic polypropylene membrane, covered with adhesive into an aqueous buffer (pH 7.4). A nicotine release rate of about 1.1 mg per square centimeter per hour was maintained for about 6 hours. FIG. 3 shows the same system without the methyl cellulose and it is observed that the release of nicotine is rapid. In FIG. 4 the methyl cellulose has been replaced by sodium lauryl sulphate, and linear nicotine release over about 4 hours was observed. FIG. 5 shows the effect of cetrimide in place of the methyl cellulose, and again a linear nicotine release over about 4 hours was observed. In FIG. 6, the effect of using Tween 20 (Registered Trade Mark) in place of methyl cellulose is shown, and release is again linear and is slower and more sustained than with the cationic or anionic surfactants. FIG. 7 shows the effect of using Celgard 3401 (Registered Trade Mark) which is a hydrophilic microporous polypropylene, and it is seen that nicotine release is exponential, not linear.

In another aspect, the invention provides an occlusive body for the transdermal administration of a physiologically active substance, the occlusive body comprising a reservoir containing said active substance preferably in liquid form, a wall of the reservoir being permeable to said active substance and the reservoir additionally containing Tea Tree Oil or a major component thereof.

Typically the dosage rate (i.e. the rate of passage of the active substance through the membrane with time) will vary by ±10% or less (preferably ±5% or less) until at least 25% (preferably at least 50%) of the active substance originally in the reservoir has passed through the membrane.

It is envisaged that the filler material may be a gel-forming substance which transforms the reservoir contents to a gel, or it may be a porous material which absorbs the reservoir contents.

The active material to be delivered by the occlusive body of the invention may be nicotine, which has been used in the experiments described below. But it is envisaged that the occlusive patch may be used to deliver other pharmacologically active substances in an aqueous medium which may contain a water- and oil-miscible solvent for the drug such as ethanol, benzyl alcohol, hexanol, butanol or alkoxy alkanols of up to $C_8$ (MW=147) for example. Drugs which it may be possible to deliver using the occlusive body include methacin in a quinoline or pyridine buffer, beta-ionone, fentanyl and pethidine or ephidrine in an aqueous medium containing a suitable drug solvent. The solvent may also be an enhancer, or an enhancer having the required miscibility may be added. Such enhancers may include oleic acid or other pharmaceutically acceptable material.

Preferably the physiologically active substance is present together with at least one diluent so that the physiologically active substance comprises no more than 25% by weight of the contents of the cavity defined between the cavity and the impermeable backing.

The membrane may optionally be composed of a multi-ply material. Only the inner layer of such a membrane needs to be hydrophobic (in the case that the reservoir contents are hydrophilic) or hydrophilic (in the case that the reservoir contents are hydrophobic). Thus in one embodiment a further permeable membrane is in contact with the exterior surface of the microporous membrane and said permeable membrane has wetting properties which are the same as or different from the wetting properties of said microporous membrane.

It is believed that the greater the difference in wetting properties between the reservoir material and the membrane (or the innermost layer of the membrane if a multi-ply membrane is used), the wider the range of useful solvents and the more linear the release of the drug. Accordingly it is desirable to employ either a strongly hydrophobic or a strongly hydrophilic microporous membrane, in conjunction with, strongly hydrophilic reservoir contents and strongly hydrophobic reservoir contents respectively.

The occlusive body may for example have an outer layer of an impervious material such as a layered aluminium foil or other metal or plastics laminate to prevent seepage or leaching of the contents of the reservoir, which is further contained by the membrane as indicated above. The reservoir side of the membrane may be faced with an area-reducing mesh formed, for example, by a non-woven fabric or by a perforated impermeable material such as aluminium foil. Suitable membrane materials are hydrophobic and microporous, for example Celgard (Registered Trade Mark) 2500 polypropylene of thickness 0.025 mm (1 mil) and pore size 0.4–0.04 microns. The face of the membrane distant from the reservoir is coated with a layer of adhesive of typical thickness about 30 micrometers, which may be any suitable dermatologically acceptable pressure sensitive adhesive that does not react chemically with the reservoir contents or prevent passage of the active material through the membrane from being rate-controlling. Thus the active material should pass reasonably rapidly through the adhesive layer, though some retardation may be acceptable in practice. The adhesive may suitably be an elastomeric silicone polymer. A protective sheet of release coated paper or other material will usually cover the adhesive layer until the pad is to be used.

It is to be understood that in the preferred article of the present invention, an adhesive layer is the means for attaching the body to the skin. However, a separate bandage material may be employed to attach the transdermal delivery system of the present invention to the skin.

For use with aqueous media in the reservoir, the membrane is preferably hydrophobic, in which case the reservoir contents may be made hydrophilic by addition of a surface active agent, which may be an anionic surface active agent e.g. sodium lauryl sulphonate, a cationic surface active agent e.g. cetrimide or a non-ionic surface active agent such as Tween 20 (Registered Trade Mark).

It is a further subsidiary or preferred object of the invention to provide an occlusive patch containing a physiologically active substance in a reservoir, in which a gel structure of the contents reduces abrupt absorption of the active substance in the event of sudden failure of the reservoir and release of the contents onto the skin. In order to solve that subsidiary problem, the viscosity of the reservoir contents is desirably high enough that they are resistant to spreading in the event of reservoir puncture, which is important from the standpoint of safety. Methyl cellulose in water is an advantageous material to use because it can perform the dual functions of surface active agent (to enhance the hydrophilicity of the reservoir contents) and viscosity modifier or gel former. When used in association with nicotine, a methyl cellulose content of about 5–6% by weight, is satisfactory. The proportion of nicotine in the reservoir material may be less than 25% by weight of the reservoir contents and desirably from 2 to 10% by weight, preferably 4 to 6%. With this relatively dilute nicotine concentration, the dose present in each reservoir is more easily controllable, the product is easier to manufacture, and to change to meet the requirements of different patch designs.

The nicotine or other pharmacologically active substance may for example be mixed with up to 2% (typically about 1% by weight) of oil of *Melaleuca Alternifolia* (Tea Tree Oil) or another bactericide before being introduced into the gel material to be filled into the reservoir. The Tea Tree oil may also be mixed with an adhesive to form a layer covering a face of the membrane remote from the reservoir as described below. The major constituents of Tea Tree Oil are 1-terpinen-4ol and terpinene with minor amounts of 1,8 cineole and p-cymene, and its properties, together with those of other Australian essential oils, are described by M. F. Beylier, *Perfumer & Flavorist*, 4, 23 (April/May 1979). Tea Tree Oil may be substituted by other essential oils that possess antibacterial qualities. Preferably the Tea Tree Oil is present in an amount of from 0.05% to 2% by weight of the liquid contents of the cavity.

In this invention, the membrane may for example be a hydrophobic microporous material such as hydrophobic microporous polypropylene or polyethylene. The reservoir contents are preferably a wetting agent water based gel formed, for example, by methyl cellulose. It has been found experimentally in vitro that the combination of a hydrophobic microporous polypropylene membrane and a water-based gel containing about 5% of methyl cellulose gives a linear or zero order release of other products such as nicotine, whilst retaining water and solids. The existence of the desirable zero-order characteristics is believed to be at least partially independent of the area of the reservoir. Reservoir contents having about 5% by weight nicotine in a high viscosity water-based medium (e.g. a medium of 5% methyl cellulose content) have given of release up to 80% of capacity. In tests carried out in vitro a steady nicotine loss through the membrane of about 1.5 mg per square centimeter per hour for a period of typically about 8 hours has been measured, followed by a slow progressive reduction in release rate up to 15 hours. The desirable linear release properties are retained when a layer of silicone adhesive such as is desirably used in an occlusive bandage is applied to the outer face of the membrane.

Further preferred features are defined in the dependent claims.

Similar desirable properties are obtained when the methyl cellulose (high viscosity - BDH 29779) is replaced by high viscosity VEGUM (R. T. Vanderbilt PLC) which is another water-based gel that also acts as a wetting agent. However, linear release properties are not obtained when the gelling agent in the reservoir is changed to Carbopol which is not a hydrophilic wetting agent, nor are they obtained when the membrane is changed to a hydrophilic grade of microporous polypropylene.

In order to establish that the linear release of nicotine is not caused by gravity but is a property of the membrane that is "chromatographic", a sample was enclosed in a blank and immersed sideways in a buffer solution. Although there was a risk of a non-meaningful result being obtained as a result of back-diffusion of the buffer through the membrane into the reservoir, a straight line release with time was in fact obtained.

In order to establish that the gel material within the reservoir was not passing through the membrane with the nicotine, a mixture of nicotine and methyl cellulose gel containing 5% by weight of nicotine was assayed for nicotine content which was found to be about 5% in a 10 mg sample. After about 2 mg of nicotine had released into an aqueous medium in an in vitro experiment, the contents of the reservoir were sampled and assayed. The reduction in the nicotine-gel ratio corresponded to the amount of nicotine released from the reservoir and was inconsistent with the simultaneous release of other materials including water therefrom. It is believed that the non-passage of the gel material through the pores of the microporous membrane results from the hydrophilic nature of the gel material combined with the hydrophobic nature of the membrane.

It will normally be expedient to dissolve the physiologically active substance in an appropriate pharmaceutically acceptable vehicle, which will carry the active substance through the reservoir membrane. Furthermore, it will normally be convenient to employ a hydrophobic membrane and hydrophilic reservoir contents. Typically, the most useful hydrophilic material will be a gel-forming surface active agent such as methyl cellulose mixed with water. This provides the additional function of immobilising the reservoir contents as noted above.

The rate of delivery of the active substance through the membrane into the blood stream of the subject can be varied as follows:

(i) by varying the surface area, the thickness and the composition of the reservoir membrane;

(ii) by varying the weight ratio of active substance: vehicle;

(iii) by varying the hydrophilicity of the reservoir contents.

Thus the dosage rate can be varied over a wide range by suitable adjustment of various parameters of the occlusive body, whilst maintaining a substantially uniform dosage rate. However, in order to minimise variations in dosage rate between different patients owing to variations in their skin resistance, the permeability of the reservoir membrane is preferably slightly less than the permeability of the least permeable skin likely to be encountered in the use of the invention and may for example be 75% to 90% of the permeability of the most resistant skin.

We claim:

1. An occlusive body for the transdermal administration of a physiologically active substance, said body comprising the combination of:
   a) an impermeable backing;
   b) a rate-controlling microporous membrane, said impermeable backing and rate-controlling microporous membrane defining a cavity therebetween;
   c) a liquid material, comprising said physiologically active substance in liquid form, confined between said impermeable backing and said rate-controlling microporous membrane within said cavity;
   d) a viscous flowable gel material confined between said impermeable backing and said rate-controlling microporous membrane within said cavity for substantially immobilizing said liquid material; and
   e) means for attaching the body to the skin, which means does not substantially affect release of said substance through said microporous membrane,
   said rate-controlling microporous membrane being permeable to and in contact with said physiologically active substance and wherein either,
   i) the rate-controlling microporous membrane is hydrophilic and the material in said cavity is hydrophobic, or
   ii) the rate-controlling microporous membrane is hydrophobic and said cavity contains a hydrophilic wetting agent,
   whereby in use, passage of said physiologically active substance through said microporous membrane is rate-controlling and said physiologically active substance is released from said rate-controlling microporous membrane at a rate that is substantially constant over a period of hours.

2. An occlusive body according to claim 1, wherein said rate-controlling microporous membrane has an exterior surface thereof coated with an adhesive.

3. An occlusive body according to claim 2, wherein said adhesive is a silicone-based adhesive.

4. An occlusive body according to claim 1, wherein said rate-controlling microporous membrane is hydrophobic and said cavity contains a hydrophilic wetting agent.

5. An occlusive body according to claim 4, wherein said cavity contains water and a surfactant, said surfactant being selected from a viscosity modifier and a gelling agent.

6. An occlusive body according to claim 5, wherein said surfactant comprises methyl cellulose.

7. An occlusive body according to claim 1, wherein said physiologically active substance is nicotine.

8. An occlusive body according to claim 7, wherein the amount of nicotine present is from 2% to 10% by weight of the total liquid contents of said cavity.

9. An occlusive body for the transdermal administration of a physiologically active substance, said body comprising the combination of:
   a) an impermeable backing;
   b) a rate-controlling microporous membrane, said impermeable backing and rate-controlling microporous membrane defining a cavity therebetween;
   c) a liquid material, comprising said physiologically active substance in liquid form, confined between said impermeable backing and said rate-controlling microporous membrane within said cavity; and
   d) a viscous flowable gel material confined between said impermeable backing and said rate-controlling microporous membrane within said cavity for substantially immobilizing said liquid material,
   said rate-controlling microporous membrane being permeable to and in contact with said physiologically active substance and wherein either,
   i) the rate-controlling microporous membrane is hydrophilic and the material in said cavity is hydrophobic, or
   ii) the rate-controlling microporous membrane is hydrophobic and said cavity contains a hydrophilic wetting agent,
   wherein said cavity contains Tea Tree Oil.

10. An occlusive body according to claim 1, wherein said cavity contains a diluent for said physiologically active substance and said physiologically active substance comprises up to 25% by weight of the total contents of said cavity.

11. An occlusive body for the transdermal administration of a physiologically active substance, said body comprising the combination of:
   a) an impermeable backing;
   b) a rate-controlling permeable membrane capable of chemically adsorbing and desorbing said physiologically active substance, said rate-controlling permeable membrane and impermeable backing defining a cavity therebetween;
   c) liquid material comprising said physiologically active substance in liquid form confined between said impermeable backing and said rate-controlling permeable membrane within said cavity;
   d) viscous flowable gel material confined between said impermeable backing and said permeable membrane within said cavity for substantially immobilizing said liquid material; and e) means for attaching the body to the skin, which means does not substantially affect release of said substance through said permeable membrane, said membrane and liquid material being selected from the group consisting of:

i) the permeable microporous membrane being hydrophilic and the material in said cavity being hydrophobic, and ii) the rate-controlling permeable membrane being hydrophobic and said cavity containing a hydrophilic wetting agent, whereby, in use, passage of said physiologically active substance through said permeable membrane is rate-controlling and said physiologically active substance is released from said permeable membrane at a rate that is substantially constant over a period of hours.

12. An occlusive body according to claim 11, wherein said rate-controlling permeable membrane has an exterior surface thereof coated with an adhesive.

13. An occlusive body according to claim 12, wherein said adhesive is a silicone-based adhesive.

14. An occlusive body according to claim 11, wherein said rate-controlling permeable membrane is hydrophobic and said cavity contains a hydrophilic wetting agent.

15. An occlusive body according to claim 14, wherein said cavity contains water and a surfactant, said surfactant being selected from a viscosity modifier and a gelling agent.

16. An occlusive body according to claim 15, wherein said surfactant comprises methyl cellulose.

17. An occlusive body according to claim 16, wherein the methyl cellulose is present in an amount of about 5% to 6% by weight relative to the contents of said cavity.

18. An occlusive body according to claim 11, wherein said physiologically active substance is selected from the group consisting of nicotine, timolol, paracetamol, ephedrine, fentanyl, cloridine, hyoscine, oestradiol, progesterone, salbutamol and testosterone.

19. An occlusive body according to claim 18, wherein said physiologically active substance is nicotine and is present in an amount of from 2% to 10% by weight of the total liquid contents of said cavity.

20. An occlusive body for the transdermal administration of a physiologically active substance, said occlusive body comprising the combination of:

a) an impermeable backing;

b) a rate-controlling permeable membrane capable of chemically adsorbing and desorbing said physiologically active substance, said rate-controlling permeable membrane and impermeable backing defining a cavity therebetween;

c) liquid material comprising said physiologically active substance in liquid form confined between said impermeable backing and said rate-controlling microporous membrane within said cavity; and d) viscous flowable gel material confined between said impermeable backing and said permeable membrane within said cavity for substantially immobilizing said liquid material, said membrane and liquid material being selected from the group consisting of:

i) the permeable membrane being hydrophilic and the material in said cavity being hydrophobic; and ii) the rate-controlling permeable membrane being hydrophobic and said cavity containing a hydrophilic wetting agent, wherein said cavity contains Tea Tree Oil.

21. An occlusive body according to claim 20, wherein the Tea Tree Oil is present in an amount of from 0.05% to 2% by weight of the total liquid contents of said cavity.

22. An occlusive body according to claim 11, wherein said impermeable backing comprises laminate selected from metal and plastics laminates.

23. An occlusive body according to claim 11, wherein said cavity contains a diluent for said physiologically active substance and said physiologically active substance comprises up to 25% by weight of the total contents of said cavity.

24. An occlusive body for the transdermal administration of a physiologically active substance, the occlusive body comprising a reservoir containing said physiologically active substance, a wall of said reservoir being permeable to said physiologically active substance and said reservoir additionally containing an additive selected from Tea Tree Oil and a major component of Tea Tree Oil.

25. An occlusive body according to claim 24, wherein said physiologically active substance is nicotine.

26. A method of transdermal administration of a physiologically active substance comprising applying to the skin or a buccal membrane of a subject the microporous membrane of an occlusive body as claimed in claim 1.

27. A method of transdermal administration of nicotine comprising applying to the skin of a subject the microporous membrane of an occlusive body as claimed in claim 7.

28. A method of transdermal administration of a physiologically active substance comprising applying to the skin or a buccal membrane of a subject the permeable membrane of an occlusive body as claimed in claim 11.

29. A method as claimed in claim 28, wherein said physiologically active substance is selected from the group consisting of nicotine, timolol, paracetamol, ephedrine, fentanyl, cloridine, hyoscine, oestradiol, progesterone, salbutamol and testosterone.

30. A method of transdermal administration of a physiologically active substance comprising applying to the skin of a subject the permeable membrane of an occlusive body as claimed in claim 24.

31. A method as claimed in claim 30, wherein said physiologically active substance is nicotine.

32. A method of transdermal administration of a physiologically active substance comprising applying to the skin or a buccal membrane of a subject the microporous membrane of an occlusive body as claimed in claim 5.

33. A method of transdermal administration of a physiologically active substance comprising applying to the skin or a buccal membrane of a subject the permeable membrane of an occlusive body as claimed in claim 15.

* * * * *

UNITED STATES PATENT AND TRADEMARK OFFICE
CERTIFICATE OF CORRECTION

PATENT NO. : 5,254,346

DATED : October 19, 1993

INVENTOR(S) : John Mark TUCKER

It is certified that error appears in the above-identified patent and that said Letters Patent is hereby corrected as shown below:

On title page, item [76], should read --JOHN MARK TUCKER-- instead of "MARK J. TUCKER".

Signed and Sealed this

Twenty-first Day of February, 1995

Attest:

BRUCE LEHMAN

Attesting Officer

Commissioner of Patents and Trademarks